United States Patent [19]
Michelson

[11] Patent Number: 5,531,749
[45] Date of Patent: Jul. 2, 1996

[54] SPINAL BONE WAXER

[75] Inventor: Gary K. Michelson, 438 Sherman Canal, Venice, Calif. 90291

[73] Assignee: Gary K. Michelson, Venice, Calif.

[21] Appl. No.: 336,556

[22] Filed: Nov. 9, 1994

Related U.S. Application Data

[63] Continuation of Ser. No. 74,780, Jun. 10, 1993, abandoned.
[51] Int. Cl.⁶ .................................................. A61B 17/00
[52] U.S. Cl. ............................................................. 606/93
[58] Field of Search .................................. 606/86, 92, 93, 606/167, 176, 84, 85; 604/289, 290, 293, 309; 15/236.01, 236.05, 236.06, 236.07, 236.08, 236.09, 105, 245.1; 451/557; 29/81.17, 81.11

[56] References Cited

U.S. PATENT DOCUMENTS

| 1,089,595 | 3/1914 | Sopha | 604/289 |
|---|---|---|---|
| 2,233,811 | 3/1941 | Doty | 604/289 |
| 2,606,364 | 8/1952 | Gustafson | 15/245.1 |
| 3,267,506 | 8/1966 | Van Patten | 15/236.07 |
| 3,820,185 | 6/1974 | Phillips | 15/236.07 |
| 5,108,403 | 4/1992 | Stern | 606/93 |

Primary Examiner—Tamara L. Graysay
Attorney, Agent, or Firm—Lewis Anten; Amedeo Ferraro

[57] ABSTRACT

A surgical spinal waxer is disclosed with a plurality of differently contoured surfaces for applying bone wax to a number of differently contoured portions of lamina in the spine. The different surfaces include a concave surface, a convex surface, two flat side surfaces, at least one which has a depression for holding bone wax and at least one which has an abraded area, a butted flat pushing surface, and a flat top surface. The shapes and dimensions of the different surfaces all correspond to the anatomy of the spinal canal.

41 Claims, 4 Drawing Sheets

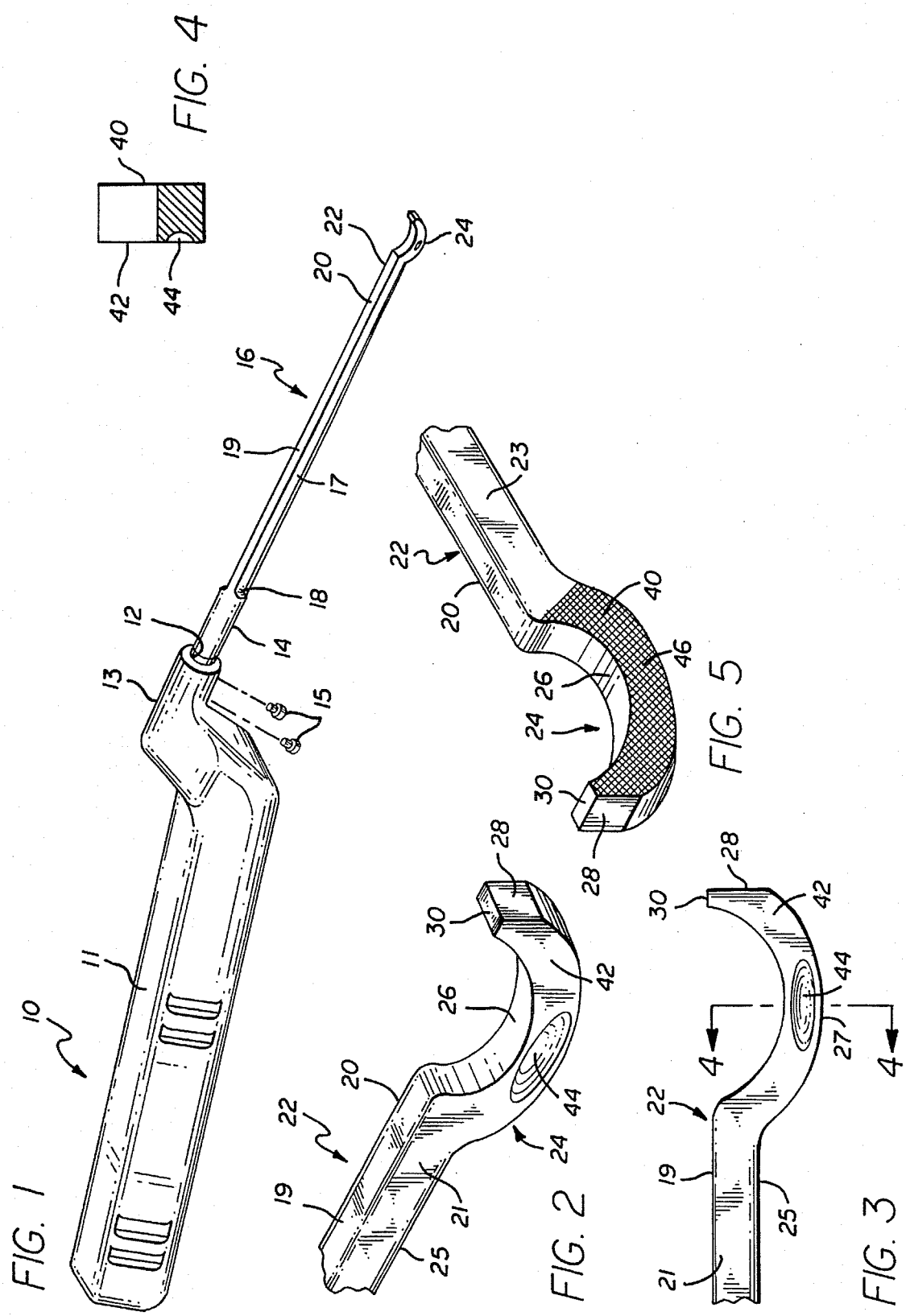

5,531,749

SPINAL BONE WAXER

This application is a continuation of application Ser. No. 08/074,780, filed on Jun. 10, 1993, now abandoned.

BACKGROUND OF THE INVENTION

1. Field of the Invention

The present invention relates to surgical instruments for use in performing human spinal surgery, and more particularly to surgical instruments for the application of bone wax to the raw, bleeding, bony surfaces of the spine.

2. Description of the Related Art

Surgery of the spine generally involves the cutting and removal of at least some bone. Bone has a hard cortical casing and a cancellous intersubstance, frequently referred to as bone marrow. As would be expected, the bone marrow is highly vascular and tends to bleed when cut. Such bleeding is frequently abated during surgery by the use of a substance called bone wax.

Bone wax is a commercially available substance which seals the open pores of the exposed marrow bone. However, because the bleeding bone is located within the depths of the wound it is generally necessary to employ a surgical instrument to apply the bone wax to the bony surface. At present, everything from the surgeon's finger, to a rolled up piece of fabric, to the use of any of a large variety of dissectors, dental tools, and other assorted instruments, are used in an attempt to apply wax to the affected area. However, because these instruments are not specifically designed for this purpose they tend to be crude and inaccurate in their ability to effectively and easily apply wax to the bleeding surface without causing further damage.

Furthermore, the previously available instruments are ineffective in transporting the bone wax to the appropriate site and because of the lack of conformity between the instrument's shape and the shape of the bone to which the bone wax should be applied, the bone ends up only partially waxed and most of the bone wax itself ends up falling within the spinal canal. Bone wax in the spinal canal can act as a foreign body and elicit an inflammatory reaction which would be injurious to the patient.

SUMMARY OF THE PRESENT INVENTION

The present invention is a surgical instrument designed for the effective transportation and application of bone wax to the human spine during surgery for controlling bleeding induced by the requisite removal of portions of bone. The surgical instrument of the present invention comprises a working waxer tip having a plurality of differently shaped and contoured surfaces each designed to congruently correspond to one of the various possible configurations of bone requiring the application of wax.

In the preferred embodiment, the working waxer tip of the present invention comprises six surfaces, including a convex surface, a concave surface, an abrader surface, a flat top surface, a butted surface, and a flat surface having a depression for the storage of bone wax. The working waxer tip is of such a size as to easily fit within the spinal canal and the surfaces of the waxer tip all correspond to the shapes and dimensions of the anatomy of the vertebral structures.

OBJECTS OF THE PRESENT INVENTION

It is an object of the present invention to provide a surgical instrument which is safer to use in applying bone wax within the spinal canal.

It is another object of the present invention to provide a surgical instrument which is more efficient in applying bone wax within the spinal canal.

It is still another object of the present invention to provide a surgical instrument which is more effective in applying bone wax within the spinal canal.

These and other objects of the present invention may be observed by reviewing the following specification and the accompanying drawings.

BRIEF DESCRIPTION OF THE DRAWINGS

FIG. 1 is a perspective view of the bone waxer affixed to a bayonet handle.

FIG. 2 is an enlarged expanded perspective right view of the universal working waxer tip.

FIG. 3 is a right side view of the working waxer tip.

FIG. 4 is a sectional view of the working waxer tip viewed along lines 4—4 of FIG. 3.

FIG. 5 is a left perspective view of the working waxer tip.

DETAILED DESCRIPTION OF THE PREFERRED EMBODIMENT

Figure 6:
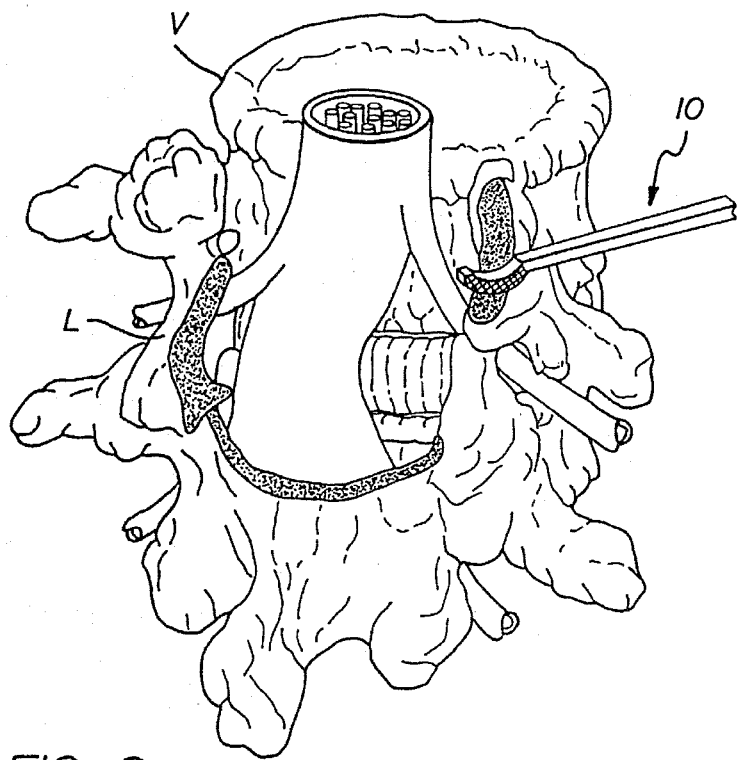
FIG. 6 is a diagrammatic view of the waxer being shown applying wax held by the waxer to the cut lamina of a cut vertebrae.

Referring to FIG. 1, the spinal bone waxer 10 of the present invention is shown as having a generally rectangular handle 11 having an opening 12 extending from a flange 13 at one end for receiving the upper end 14 of shaft 16. The flange 13 is positioned so as to hold the shaft 16 at an angle of approximately 15 degrees from the longitudinal axis of the handle 11 so as to not interfere with visual inspection of the working waxer tip 24 of the shaft of the instrument when in use. The shaft 16 is cylindrical at its upper end 14. Screws 15 pass through openings (not shown) in flange 13 to engage the upper end 14 of shaft 16 in order to hold the shaft 16 fixed relative to the handle 11.

The shaft 16 converges at transition 18 to a generally rectangular portion 17 having slightly beveled edges 20 and terminates at its convex lower surface 27 in a working waxer tip 24. The rectangular portion 17 has a top wall 19, side walls 21 and 23 and bottom wall 25.

Referring to FIGS. 2-5, the detailed structure of the working waxer tip 24 is shown.

The working waxer tip 24 consists of a generally arcuate concave upper surface 26, a convex lower surface 27, a flat butted end surface 28 substantially perpendicular to the central axis of the shaft 16, a top surface 30 perpendicular to the butted end surface 28, having its plane substantially on line with the top wall 19 of the shaft 16, and side surfaces 40 and 42. The side surfaces 40 and 42 of working waxer tip 24 are on the same plane and extensions of as the side walls 21 and 23 of rectangular portion 17 of shaft 16. Side surface 42 of the working waxer tip 24 includes an elongated oval depression 44 for holding bone wax. The other side surface 40 of working waxer tip 24 has an abrasive cross hatching 46, used for scraping.

In the preferred embodiment, the handle is approximately 4¾ inches (120.65 mm) long, ⅝ inches (15.88 mm) wide, and ⅝ inches (15.88 mm) thick. The shaft 16 is approximately 4¼ inches (107.95 mm) long. The working waxer tip is about ¼ (6.35 mm) inches long, ⅛ inches (3.175 mm) wide and has an overall height from the convex lower surface to the top of the flat butted end surface 28 of approximately ⅛ inches (3.175 mm). The flat butted end surface 28 has a height of about ⅛ inches (3.75 mm), while top surface 30 has a depth of about 1/16 inches (1.59 mm). The concave upper surface 26 has a depth of about 1/16 inches (1.59 mm). The depression 44 is approximately 1/32 inches (0.79 mm) deep, and has a length of 1/16 inches (1.75 mm) and a width of 1/32 inches (0.79 mm).

The above dimensions are those applicable to a bone waxer for use in the lumbar spine. A bone waxer for use in the cervical spine would have dimensions approximately one half of those recited above.

Referring to FIGS. 6–10, the present invention is used as follows: After the surgeon has cut the lamina (L) of the vertebra (V), as shown in FIGS. 6–10, a small amount of bone wax is inserted in the depression 44. Bone wax will adhere to any of the surfaces, but if an increased amount of bone wax is desired to be used, a ball of bone wax can be held in the depression for applying bone wax to a number of segments of cut lamina. As more bone wax is needed, bone waxer 10 is removed from the wound, and additional bone wax inserted in the depression 44 or applied to the working waxer tip 24. The bone wax may also be applied by using any of the other surfaces of the working waxer tip 24.

Figure 7:
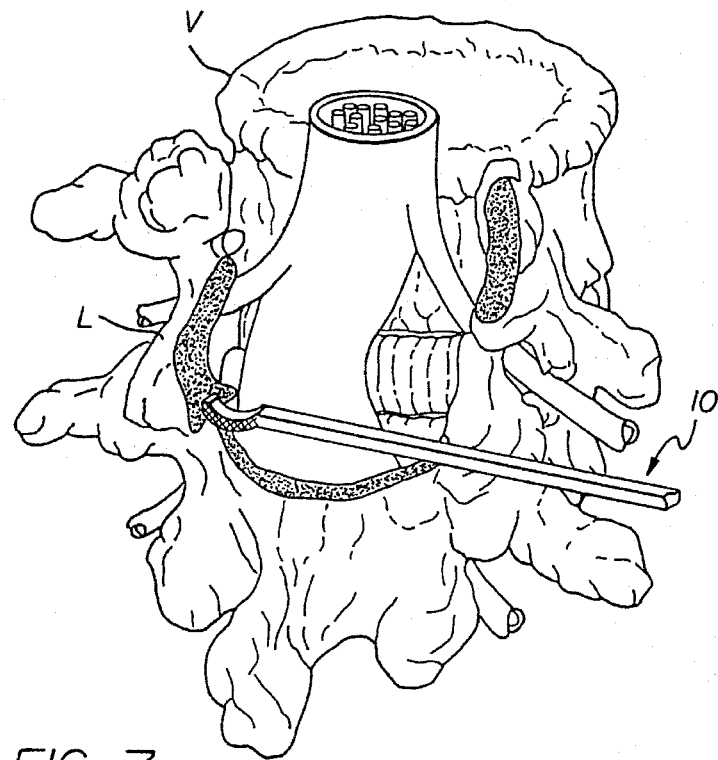
FIG. 7 is diagrammatic view of the waxer showing the butted end pushing wax against the cut lamina of the vertebrae.
Figure 10:
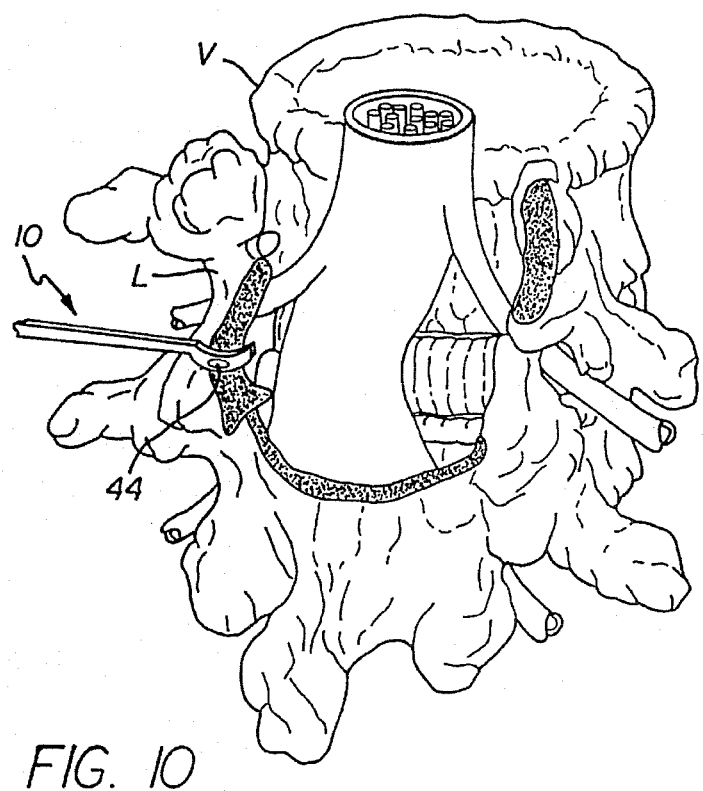
FIG. 10 is a diagrammatic view of the waxer showing the roughened and abrasive portion abrading smooth the cut laminal edge of the vertebrae.

The bone waxer 10 has a flat butted end surface 28 to press wax onto the canal floor which is longitudinally oriented in the horizontal plane and therefore at a right angle to the direction of approach to a surgical instrument introduced from directly above as determined by the requisite placement of the surgical incision as shown in FIG. 7. The concave upper surface 26 is oriented 90 degrees to the long axis of the shaft 16 so as to orient it a right angle to the cut surface of the lamina to whose size and shape the concavity corresponds for the application of bone wax as shown in FIG. 10. The convex lower surface 27 is also oriented 90 degrees to the long axis of the shaft 16 and is designed to facilitate the application of bone wax at the base of the spinous process which area will be concave and under cut following a routine laminotomy as shown in FIG. 7. The two flattened side surfaces 40 and 42 allow for the application of wax to vertically oriented surfaces (e.g. partially osteomized facet joint) by a rotation of the instrument as well as laterally directed pressure. The side surface 42 having the depression 44 is used to assist in the holding and delivery of the bone wax as shown in FIG. 6, while the opposite side surface 40 is flattened to facilitate the actual application of the bone wax to the bone itself, as well as a roughened abrasive cross hatching 46 which can be used to scrape the bone wax. In situations where there is a perforating vessel on a vertebral surface of the spine, bone wax is applied with the top surface 30 to plug the vessel.

Figure 8:
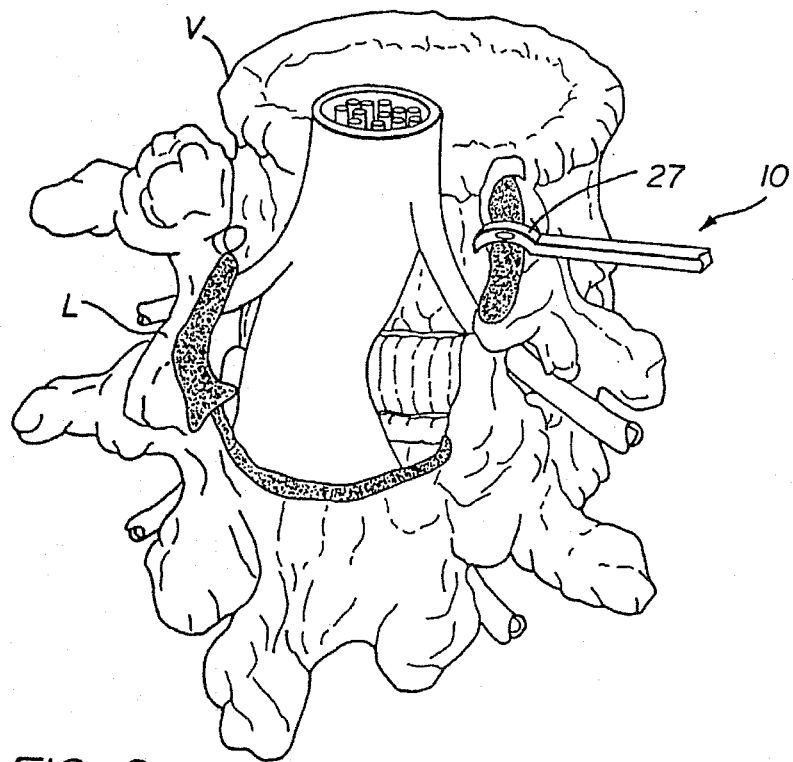
FIG. 8 is a diagrammatic view of the waxer showing the concave upper surface of the waxer applying wax to the cut lamina of the vertebrae.

Referring to FIG. 8, the concave upper surface 26 of the spinal bone waxer 10 is used to apply bone wax to the cut lamina (L) of the vertebra (V).

Figure 11:
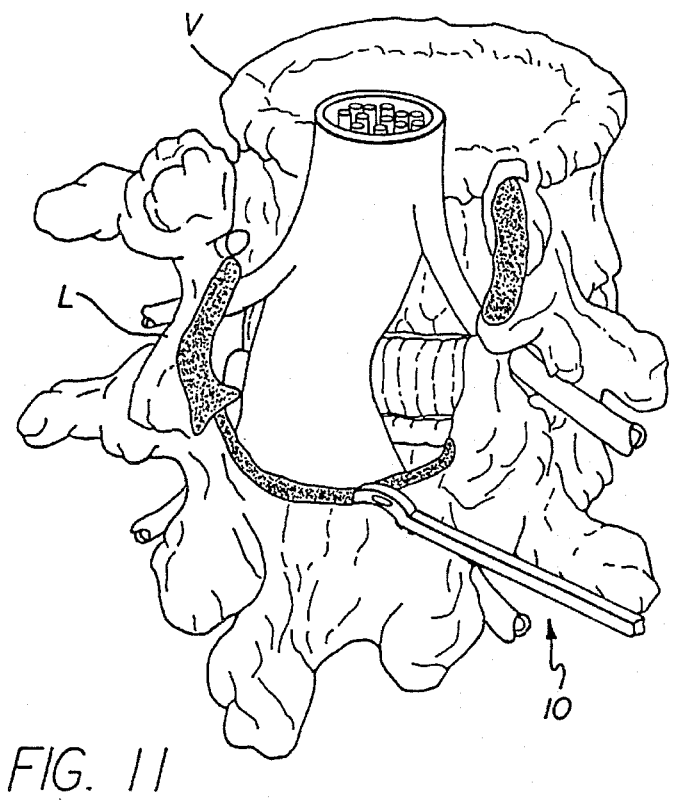
FIG. 11 is a diagrammatic view of the waxer showing the roughened and abrasive portion abrading smooth the cut lamina of the vertebrae.

Referring to FIG. 11, the bone waxer 10 is shown with the roughened abrasive cross hatching 46 of the side surface 40 of the working waxer tip 24 being used to abrade smooth the cut lamina (L) of the vertebra (V).

Figure 9:
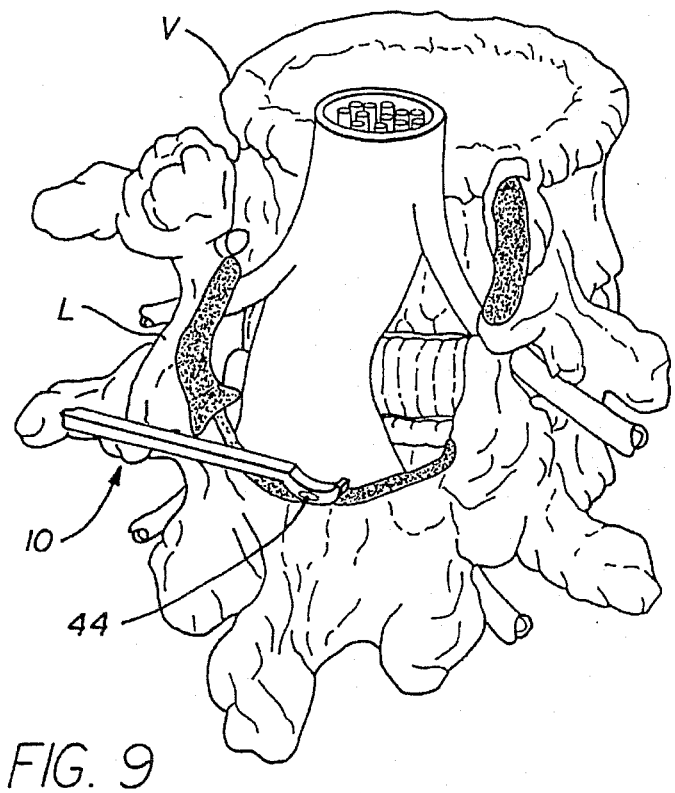
FIG. 9 is a diagrammatic view of the waxer showing the convex lower surface applying wax to the cut lamina of the vertebrae.

Referring to FIG. 9, the convex lower portion 27 of the working waxer tip 24 is used to apply wax to the cut lamina (L) of the vertebra (V).

While the above dimensions are the preferred dimensions, this may be varied without departing from the scope of the present invention. Additionally, other shapes and contours, and combinations of different shapes and contours may be used without departing from the scope of the present invention. However, the sizes must not be so large as to not be able to conveniently and safely fit within the spinal canal.

What is claimed is:

1. A spinal bone waxer comprising: a handle; a substantially rigid shaft having a longitudinal axis terminating at a substantially rigid working waxer tip, said working waxer tip having means for applying bone wax to the vertebrae of the spine, said means for applying bone wax comprising a plurality of different shaped surfaces proportionate for the purpose of applying bone wax to the vertebrae of the spine during surgery, said plurality of surfaces comprising upper and lower curved surfaces and side walls, at least one of said side walls being substantially flat.

2. The spinal bone waxer of claim 1 including an end portion, said end portion being substantially perpendicular to the longitudinal axis of the shaft.

3. The spinal bone waxer of claim 2 including a flat top surface perpendicular to said end portion.

4. A spinal bone waxer comprising a handle and shaft having a working waxer tip, said working waxer tip having upper and lower curved surfaces and side walls, at least one of said side walls and surfaces having a depression for holding wax, and at least one of said surfaces having a roughened abrasive portion.

5. A spinal bone waxer comprising:
   a handle;
   a substantially rigid shaft having a substantially rigid working waxer tip, said waxer tip having means for applying bone wax to the vertebrae of the spine, said means for applying bone wax comprising a plurality of different shaped surfaces proportionate for the purpose of applying bone wax to the vertebrae of the spine during surgery, said plurality of surfaces comprising a concave surface, a convex surface and at least one substantially flat surface.

6. The spinal bone waxer of claim 5 wherein said working waxer tip has a flattened butted end surface.

7. A spinal bone waxer comprising a handle, a shaft having a working waxer tip, said waxer tip having a concave surface, a convex surface, and at least one flat surface having a depression for holding bone wax.

8. A spinal bone waxer comprising a handle, a substantially rigid shaft having a longitudinal axis and a substantially rigid working tip, said working tip having means for applying bone wax to the vertebrae of the human spine, said means for applying bone wax having a plurality of different shaped surfaces proportionate for the purpose of applying bone wax to the vertebrae of the human spine during surgery.

9. The spinal bone waxer of claim 8 in which said plurality of surfaces include a convex surface, a concave surface, and a flat butted end surface, said flat butted end surface being perpendicular to the axis of said shaft.

10. The spinal bone waxer of claim 9 in which said plurality of surfaces further includes a flat top surface perpendicular to said butted end surface.

11. The spinal bone waxer of claim 10 in which said plurality of surfaces further includes a first flat side surface.

12. The spinal bone waxer of claim 11 in which said plurality of surfaces includes a second flat side surface.

13. The spinal bone waxer of claim 11 in which said first flat side surface includes a depression therein for transporting and applying said bone wax.

14. The spinal bone waxer of claim 8 in which at least one of said plurality of surfaces has a depression therein for transporting and applying said bone wax.

15. A spinal bone waxer comprising a handle, a shaft having a longitudinal axis and a working tip, said working tip having means for applying bone wax to the vertebrae of the human spine, said means for applying bone wax having a plurality of different shaped surfaces proportionate for the purpose of applying bone wax to the vertebrae of the human spine during surgery, said plurality of surfaces including a convex surface, a concave surface, and a flat butted end surface, said flat butted end surface being perpendicular to the axis of said shaft, a flat top surface perpendicular to said butted end surface, a first flat side surface, and a second flat side surface, said second flat side surface comprising abrading means for abrading smooth the laminar edges of said vertebrae which have been surgically cut.

16. A spinal bone waxer comprising a handle, a shaft having a longitudinal axis and a working tip, said working tip having means for applying bone wax to the vertebrae of the human spine, said means for applying bone wax having a plurality of different shaped surfaces proportionate for the purpose of applying bone wax to the vertebrae of the human spine during surgery; at least one of said plurality of surfaces comprising abrading means for abrading smooth the laminar edges of said vertebrae which have been surgically cut.

17. A spinal bone waxer comprising a handle and a substantially rigid shaft having a longitudinal axis terminating at a substantially rigid working waxer tip, said working waxer tip having a plurality of different shaped surfaces proportionate for the purpose of applying bone wax to the vertebrae of the human spine during surgery, said plurality of surfaces comprising an upper curved surface on a first side and a lower curved surface on a second opposite side, said lower curved surface being in a plane parallel to said upper curved surface, said working waxer tip terminating in a butted end having a first surface substantially perpendicular to said longitudinal axis and side walls.

18. The spinal bone waxer of claim 17 in which at least one of said side walls includes a depression for holding bone wax.

19. The spinal bone waxer of claim 17 in which said working waxer tip includes a roughened abrasive portion.

20. The spinal bone waxer of claim 17 in which said butted end includes a flat top surface perpendicular to said first flat surface.

21. The spinal bone waxer of claim 17 in which said upper curved surface is concave.

22. The spinal bone waxer of claim 17 in which said lower curved surface is convex.

23. The spinal bone waxer of claim 17 in which said shaft is tapered for improving the line of sight of the surgeon operating the spinal bone waxer.

24. A surgical instrument for the application of wax to the spine during surgery comprising: a handle; a substantially rigid shaft having an outer surface and a longitudinal axis terminating at a substantially rigid working tip, said working tip comprising: a butted surface at the distal end of said working tip, said butted surface being in a plane substantially perpendicular to said longitudinal axis; a concave surface oriented substantially parallel to and facing substantially perpendicular to said longitudinal axis, said concave surface having at least one portion offset from the outer surface of said shaft; a convex surface oriented substantially parallel to and facing substantially perpendicular to said longitudinal axis said convex surface having at least one portion offset from the surface of said shaft; a first flattened surface oriented substantially parallel to and facing substantially perpendicular to said longitudinal axis; whereby the dimensions of said handle, said shaft, and said working tip are appropriate for use in the areas of the spine.

25. The surgical instrument claim 24 in which said working tip includes a second flattened surface oriented substantially parallel to, and facing substantially perpendicular to said longitudinal axis.

26. The surgical instrument of claim 24 in which at least one of said flattened surfaces of said working tip has an irregular surface.

27. The surgical instrument of claim 26 in which said irregular surface includes means for abrading.

28. The surgical instrument of claim 24 in which said working tip has at least one surface having at least one depression suitable for holding wax.

29. The surgical instrument of claim 24 in which said concave and convex surfaces are in parallel planes and form the obverse sides of said working tip.

30. The surgical instrument of claim 24 in which at least a part of said surgical instrument is disposable.

31. The surgical instrument of claim 24 in which said entire surgical instrument is disposable.

32. The surgical instrument of claim 24 in which said butted surface is irregular.

33. The surgical instrument of claim 24 in which said tip has at least one depression for holding bone wax.

34. The surgical instrument of claim 24 in which said working waxer tip includes a roughened abrasive portion.

35. The surgical instrument of claim 24 in which said shaft is tapered for improving the line of sight of the surgeon operating said surgical instrument.

36. A spinal bone waxer comprising a handle, a substantially rigid shaft having a longitudinal axis and a substantially rigid working tip, said working tip having means for applying bone wax to the vertebrae of the human spine, said means for applying bone wax having a plurality of different shaped surfaces proportionate for the purpose of applying bone wax to the vertebrae of the human spine during surgery, said plurality of surfaces including a convex surface, a concave surface, and a flat butted end surface, said flat butted end surface being perpendicular to the axis of said shaft, said plurality of surfaces including a flat top surface perpendicular to said butted end surface, a first flat side surface, a second flat side surface, said first flat side surface including a depression therein for transporting and applying said bone wax.

37. A spinal bone waxer comprising a handle and a substantially rigid shaft having a longitudinal axis terminating at a substantially rigid working waxer tip, said working waxer tip having a plurality of different shaped surfaces proportionate for the purpose of applying bone wax to the vertebrae of the human spine during surgery, said plurality of surfaces comprising an upper curved surface on a first side and a lower curved surface on a second opposite side, said lower curved surface being in a plane parallel to said upper curved surface, said working waxer tip terminating in a butted end having a first surface substantially perpendicular to said longitudinal axis and side walls, at least one of said side walls including a depression for holding bone wax.

38. A spinal bone waxer comprising a handle and a substantially rigid shaft having a longitudinal axis terminating at a substantially rigid working waxer tip, said working waxer tip having a plurality of different shaped surfaces proportionate for the purpose of applying bone wax to the vertebrae of the human spine during surgery, said plurality of surfaces comprising an upper curved surface on a first side and a lower curved surface on a second opposite side, said lower curved surface being in a plane parallel to said upper curved surface, said working waxer tip terminating in a butted end having a first surface substantially perpendicular to said longitudinal axis and side walls, said working waxer tip including a roughened abrasive portion.

39. A surgical instrument for the application of wax to the spine during surgery comprising: a handle; a substantially rigid shaft having an outer surface and a longitudinal axis terminating at a substantially rigid working tip, said working tip comprising: a butted surface at the distal end of said working tip, said butted surface being in a plane substantially perpendicular to said longitudinal axis; a concave surface oriented substantially parallel to and facing substantially perpendicular to said longitudinal axis, said concave surface having at least one portion offset from the surface of said shaft; a convex surface oriented substantially parallel to and facing substantially perpendicular to said longitudinal axis said convex surface having at least one portion offset from the surface of said shaft; at least one flattened surface oriented substantially parallel to and facing substantially perpendicular to said longitudinal axis; whereby the dimensions of said handle, said shaft, and said working tip are appropriate for use in the areas of the spine, at least one of said flattened surfaces of said working tip having an irregular surface.

40. The surgical instrument of claim 39 in which said irregular surface includes means for abrading.

41. The surgical instrument of claim 39 in which said working waxer tip includes a roughened abrasive portion.

* * * * *